United States Patent [19]

Feigel et al.

[11] Patent Number: Plant 5,467

[45] Date of Patent: May 14, 1985

[54] ROSE CV. AROFEIGEL

[75] Inventors: John R. Feigel, Evansville, Ind.; Jack E. Christensen, Ontario, Calif.

[73] Assignee: Armstrong Nurseries, Inc., Ontario, Calif.

[21] Appl. No.: 531,255

[22] Filed: Sep. 12, 1983

[51] Int. Cl.[3] ..... A01H 5/00

[52] U.S. Cl. ..... Plt./18

[58] Field of Search ..... Plt./18

*Primary Examiner*—Robert E. Bagwill

*Attorney, Agent, or Firm*—Synnestvedt & Lechner

[57] ABSTRACT

A new and distinct variety of Rose; namely, a sport of the Rose "Century Two" characterized in that it produces flowers of significantly pink lighter coloration than "Century Two".

1 Drawing Figure

This invention relates to a new variety of rose cv. Arofeigel. The plant is a hybrid tea rose and originated as a bud sport of the rose "Century Two" (U.S. Plant Pat. No. 3,340.)

The sport was discovered by John R. Feigel growing in his garden in Evansville, Indiana and was first propagated by budding by Jack E. Christensen in Ontario, Calif. Subsequent reproduction of the plant by budding at both Wasco, Calif. and Ontario, Calif. have shown that the sport is stable in its essential characteristics and holds its distinguishing characteristics through succeeding propagations.

The accompanying drawing illustrates the new plant variety in color and shows the flowering thereof from bud to full bloom.

Throughout this specification, color names beginning with a small letter signify that the name of the color, as used in common speech is aptly descriptive. Color names beginning with a capital letter designate values based on the R.H.S. Colour Chart published by The Royal Horticultural Society, London.

The characteristics of the sport are substantially identical to those of the parent "Century Two" as described in U.S. Plant Pat. No. 3,340 except as hereinafter noted.

The general distinction between the sport and its parent is in flower coloration. The parent produces flowers of a deep pink coloration, while the sport produces flowers of significantly lighter pink coloration, essentially as described and illustrated herein.

The bud of the sport, as the calyx breaks, is between Red 39A and Red 48A; whereas in the parent at this stage, the color is much darker—about Red 53A.

As the first petal of the sport opens, the outside basal attachment zone shows a coloration of between Yellow 4A and Yellow 13C; and quickly suffuses to between Orange-Red 34C and Orange-Red 35B. Most of the remaining part of the petal is between Red 39B and Red 55B. The inside larger basal attachment zone is near Yellow 9A, and suffuses to between Orange-Red 33C and Orange-Red 35B with the remaining majority of the petal having a coloration between Red 38D and Red 56D. With the parent plant, both the inside and outside petal coloration is near Red 55A.

The paragraphs immediately following describe the color values of a newly opened bloom grown outdoors in the month of May in Ontario, Calif.

The outside surface of outside, intermediate and inside petals have the same coloration: the basal attachment zone is between Yellow 4A and Yellow 13C and quickly suffuses to a zone between Orange-Red 35B and Orange-Red 33C. The remaining majority of the petal is between Red 55B and Red-Purple 62A.

The inside surface of the outside, intermediate and inside petals is of the same coloration; a basal attachment zone is near Yellow 9A and quickly suffuses to a zone between Orange-Red 35B and Orange-Red 33C. The remaining majority of the petal is between Red 56B and Red-Purple 62D.

In contrast the outer surface of the outside petal of "Century Two" is between Red-Purple 64D and Red 55A, with a small area at the base of the petal near Yellow 5C. The inner surface of the outside petal is near Red 55A with a small area at the base of the petal near Yellow 5C.

Both the outer surface and inner surface of the intermediate petal and of the inner petal of "Century Two" is between Red 55A and Red-Purple 59D with a small area at the base of the petal near Yellow 5C.

The following description gives the color values of a rose of the Arofeigel variety that was opened three days; the rose had been grown outdoors during the month of May at Ontario, Calif.

The outside surface of the outside and inside petals have the same coloration: a basal attachment zone of near Yellow 9D suffuses evenly to between Red 56B and Red-Purple 62D.

The inside surface of the outside and inside petals is the same as the outside surface but suffuses to between Red 56B and near white.

In contrast the outer surface of the outside petal of "Century Two" was between Red-Purple 58A and Red 55A. The inner surface was between Red-Purple 64D and Red 55B. The inside petal is characterized by the same color as the outside petal, both on the outer surface and in the inner surface.

The general color effect of the newly opened Arofeigel flower is between Red 55D and Red-Purple 62B; and the bloom after being three days open is between Red 56D and Red-Purple 62D.

In contrast the general color effect of the newly opened "Century Two" flower is between Red 55A and Red-Purple 59D, and after being three days open gives a general color effect which is between Red-Purple 64D and Red 55B.

We claim:

1. A new and distinct variety of rose as a sport of the rose "Century Two" (U.S. Plant Pat. No. 3,340) characterized in that it produces flowers of significantly lighter pink coloration, essentially as described and illustrated and otherwise having the characteristics of the parent rose cv. "Century Two."

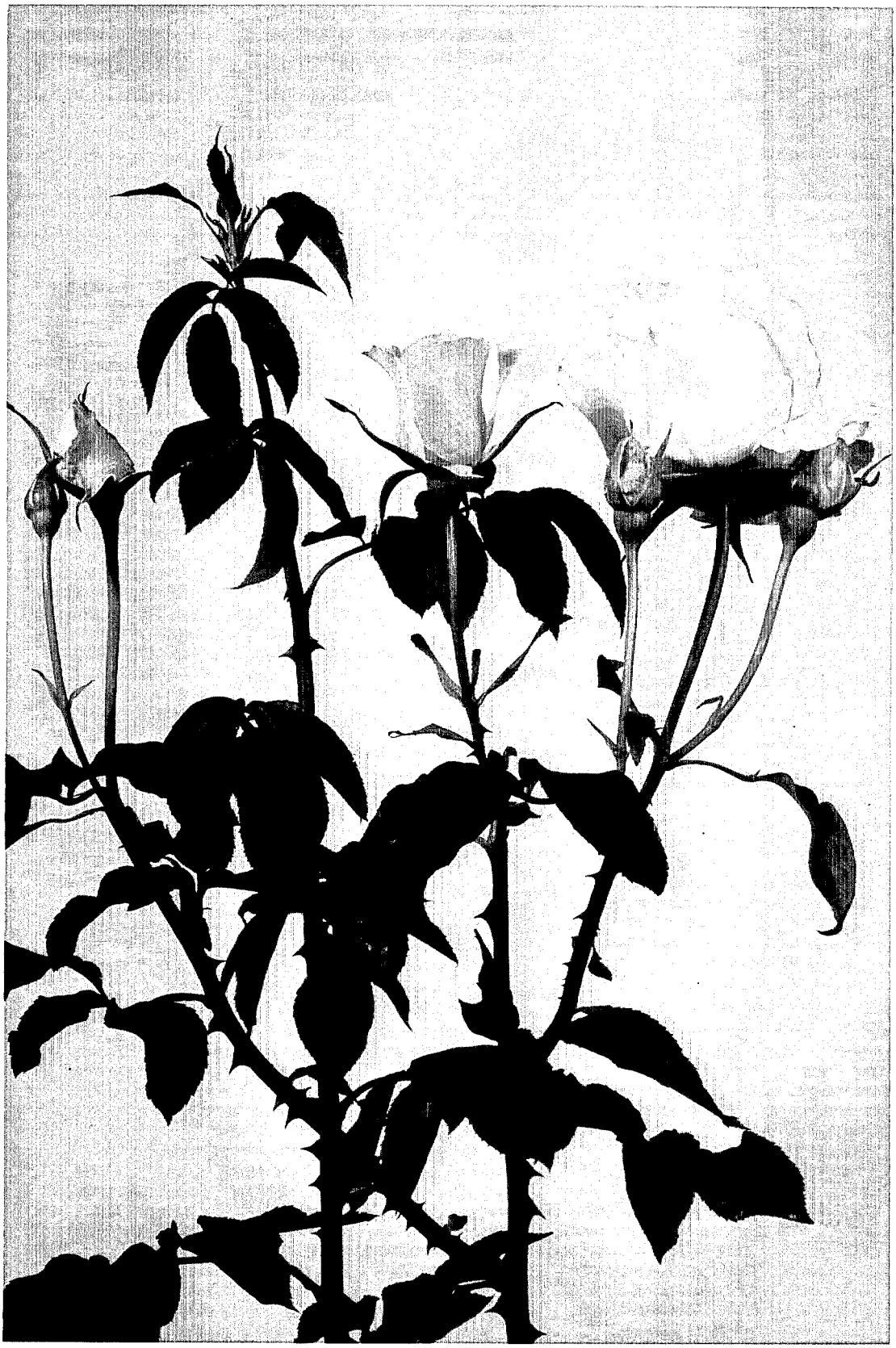

* * * * *